United States Patent
Lee (10) Patent No.: US 7,651,694 B2
(45) Date of Patent: Jan. 26, 2010

(54) THERAPEUTIC CALCIUM PHOSPHATE PARTICLES AND METHODS OF MAKING AND USING SAME

(75) Inventor: William W. Lee, San Diego, CA (US)

(73) Assignee: NOD Pharmaceuticals, Inc., San Diego, CA (US)

( * ) Notice: Subject to any disclaimer, the term of this patent is extended or adjusted under 35 U.S.C. 154(b) by 318 days.

(21) Appl. No.: 11/057,327

(22) Filed: Feb. 11, 2005

(65) Prior Publication Data

US 2005/0234114 A1    Oct. 20, 2005

Related U.S. Application Data

(60) Provisional application No. 60/544,693, filed on Feb. 13, 2004.

(51) Int. Cl.
A61K 38/28 (2006.01)
A61K 38/16 (2006.01)

(52) U.S. Cl. ............... 424/420; 514/3; 514/2; 514/23; 514/44; 424/198.1; 424/85.1; 424/85.4; 424/185.1; 530/399; 530/303; 530/351; 536/23.1

(58) Field of Classification Search .......... None
See application file for complete search history.

(56) References Cited

U.S. PATENT DOCUMENTS

| | | | |
|---|---|---|---|
| 3,925,545 A | 12/1975 | Relyveld | |
| 4,016,252 A | 4/1977 | Relyveld | |
| 4,350,686 A | 9/1982 | Relyveld et al. | |
| 4,500,512 A | 2/1985 | Barme | |
| 4,552,756 A | 11/1985 | Relyveld et al. | |
| 5,178,882 A | 1/1993 | Kossovsky et al. | |
| 5,219,577 A | 6/1993 | Kossovsky et al. | |
| 5,306,508 A | 4/1994 | Kossovsky et al. | |
| 5,334,394 A | 8/1994 | Kossovsky et al. | |
| 5,364,838 A | 11/1994 | Rubsamen | |
| 5,443,829 A * | 8/1995 | Kensil et al. ............... 424/765 |
| 5,460,830 A | 10/1995 | Kossovsky et al. | |
| 5,460,831 A | 10/1995 | Kossovsky et al. | |
| 5,462,750 A | 10/1995 | Kossovsky et al. | |
| 5,462,751 A | 10/1995 | Kossovsky et al. | |
| 5,464,634 A | 11/1995 | Kossovsky et al. | |
| 5,506,203 A | 4/1996 | Backstrom et al. | |
| 5,549,973 A | 8/1996 | Majetich et al. | |
| 5,580,859 A | 12/1996 | Felgner et al. | |
| 5,593,875 A | 1/1997 | Wurm et al. | |
| 5,595,762 A | 1/1997 | Derrieu et al. | |
| 5,620,896 A | 4/1997 | Herrmann et al. | |
| 5,629,021 A | 5/1997 | Wright | |
| 5,641,515 A | 6/1997 | Ramtoola | |
| 5,648,097 A | 7/1997 | Nuwayser | |
| 5,695,617 A | 12/1997 | Graiver et al. | |
| 5,747,001 A | 5/1998 | Wiedmann et al. | |
| 5,785,975 A | 7/1998 | Parikh | |
| 5,827,822 A | 10/1998 | Floc'h et al. | |
| 5,866,553 A | 2/1999 | Donnelly et al. | |
| 5,891,420 A | 4/1999 | Cutie | |
| 5,898,028 A | 4/1999 | Jensen et al. | |
| 5,902,789 A | 5/1999 | Stoltz | |
| 6,183,803 B1 | 2/2001 | Morcol et al. | |
| 6,355,270 B1 * | 3/2002 | Ferrari et al. ............... 424/489 |
| 6,355,271 B1 | 3/2002 | Bell et al. | |
| 2001/0048925 A1 | 12/2001 | Bell et al. | |
| 2002/0054914 A1 | 5/2002 | Morcol et al. | |
| 2002/0068090 A1 | 6/2002 | Bell et al. | |
| 2003/0004096 A1 * | 1/2003 | Boderke ............... 514/3 |
| 2003/0185892 A1 | 10/2003 | Bell et al. | |
| 2004/0258763 A1 | 12/2004 | Bell | |

FOREIGN PATENT DOCUMENTS

| | | |
|---|---|---|
| FR | 2181426 | 12/1973 |
| FR | 2466991 | 4/1981 |
| GB | 1422973 | 1/1976 |
| WO | WO-90/11092 | 10/1990 |
| WO | WO-93/17706 | 9/1993 |
| WO | WO-93/24640 | 12/1993 |
| WO | WO-98/35562 | 8/1998 |
| WO | WO-00/15194 | 3/2000 |
| WO | WO-00/46147 | 8/2000 |
| WO | WO-02/064112 | 8/2002 |
| WO | WO-03/051394 | 6/2003 |
| WO | WO-2004/050065 | 6/2004 |

OTHER PUBLICATIONS

Meunier F., New methods for delivery of antifungal agents., Rev. Infect. Dis., 11 (Suppl. 7), S1605-S1612, 1989.*

Govers et al. Characterization of the adsorption of conjugated and unconjugated bile acids to insoluble, amorphous calcium phosphate. J. Lipid Res. 35, 741-748, 1994.*

(Continued)

Primary Examiner—Lorraine Spector
Assistant Examiner—Elly-Gerald Stoica
(74) Attorney, Agent, or Firm—Morrison & Foerster LLP (57) ABSTRACT

The present invention provides calcium phosphate nano-particles encapsulated with biologically active macromolecules. The particles may be used as carriers of biologically active macromolecule for delivery of the macromolecules. The invention also provides methods of making and using the particles.

25 Claims, 6 Drawing Sheets

OTHER PUBLICATIONS

Beyger et al., J. Pharm. Sci. (1986) 75:573-578.
Carino et al., Controlled Release (2000) 65:261.
Chen et al., Mol. Cell. Biol. (1987) 7:2745-2752.
Cherian et al., Drug Development and Industrial Pharmacy (2000) 26:459-463.
Damge et al., Diabetes (1988) 37:246.
Desai et al., Pharm. Res. (1996) 13:1838.
Hussain et al., Adv. Drug Delivery Rev. (2001) 50:107.
Jani et al., J. Pharm. Pharmacol. (1990) 42:821.
Jordan et al., Nucleic Acids Research (1996) 24:596-601.
Loyter et al., Exp. Cell Res. (1982) 139:223-234.
Maharaj et al., J. Pharm. Sci. (1984) 73:39-42.
Morcol et al., Int'l. J. Pharmaceutics (2004) 277:91.
Pan et al., Int'l. J. Pharmaceutics (2002) 249:139.
Roy et al., Int'l. J. Pharmaceutics (2003) 250:25.
Welzel et al., J. Mater. Chem. (2004) 14:2213-2217.
First Office Action for Chinese Patent Application No. 200580012351.3, issued Aug. 8, 2008, 3 pages.
Yang, The Growth Patterns of Calcium Phosphate Precipitation in Gel System, Chinese Journal of Inorganic Chemistry (2002) 18(5):523-524 (with English Abstract).

* cited by examiner

THERAPEUTIC CALCIUM PHOSPHATE PARTICLES AND METHODS OF MAKING AND USING SAME

CROSS-REFERENCE TO RELATED APPLICATIONS

This application claims the priority benefit of the provisional patent application U.S. Ser. No. 60/544,693, filed Feb. 13, 2004, which is incorporated herein by reference in its entirety.

STATEMENT REGARDING FEDERALLY SPONSORED RESEARCH OR DEVELOPMENT

Not applicable.

FIELD OF THE INVENTION

The present invention relates to novel calcium phosphate particles, methods of making them, and methods of using them as carriers for delivery of biologically active macromolecules.

BACKGROUND OF THE INVENTION

Macromolecule pharmaceutical, including proteins, peptide, polysaccharide, nucleic acid, lipids or the combination, are an increasingly important class of drugs to treat various medical conditions. The primary route for administrating macromolecular pharmaceuticals is injection, which is unpleasant, expensive and often results in poor patient compliance. Oral delivery is a preferred route to administer medicine. However, macromolecular drugs are poorly absorbed through intestines and can be easily destroyed by stomach acid or gastrointestinal enzymes. A promising approach to overcome the barriers for oral macromolecule delivery is to use nano-particles, which may offer protection from degradation and enable absorption of macromolecule drugs.

It has been reported that nano-particles loaded with insulin can be used to deliver bioactive insulin to animals. For example, prevention of plasma glucose elevation by insulin loaded into poly(lactide-co-glycolide) nano-particles with fumaric anhydride oligomer and iron oxide additives has been shown. Carino et al, Controlled Release 65:261, (2000). Another example of oral delivery of insulin with Chitosan nano-particles is provided by Pan et al., Intl. J. Pharmaceutics, 249:139, (2002). In addition, polyalkylcyanoacrylate nanocapsules have also been reported to be an effective carrier for oral delivery of insulin in diabetic animals. Damge et al. Diabetes, 37:246, (1988). The uptake of particulate materials by gastrointestinal route is documented and lymphatic Peyer's patches are involved. Hussain et al., Adv. Drug Delivery Rev. 50:107, (2001).

Among the factors affecting absorption of particles, particle size appears to be the primary factor. For example, Jani et al. (J. Pharm. Pharmacol. 42:821, 1990) studied the intestinal absorption of polystyrene particles of various sizes in rats. The absorption efficiency of polystyrene particles is clearly depending on the size. Particles less than 100 nm showed significant absorption, while large particles (500 nm or more) only showed moderate to low absorption.

The size dependence on particle intestinal absorption is also observed in poly(lactide-co-glycolide) or PLGA particles by Desai et al. (Pharm. Res. 13:1838, 1996). In this study, PLGA particles larger than 500 nm showed virtually no uptake via intestinal tract, yet 36% of PLGA particle of 100 nm was absorbed.

Nanometer scale particles have been proposed for use as carrier particles for biological macromolecules such as proteins and nucleic acids. See U.S. Pat. Nos. 5,178,882; 5,219,577; 5,306,508; 5,334,394; 5,460,830; 5,460,831; 5,462,750; 5,464,634, 6,355,271.

Calcium phosphate particles are bio-adhesive/biocompatible and have been routinely used as carrier to deliver nucleic acid into intracellular compartments in vitro. Chen et al., Mol. Cell. Biol. 7:2745-52, (1987); Welzel et al., J. Mater. Chem. 14:2213-2217 (2004); Jordan et al., Nucleic Acids Research 24:596-601 (1996); Loyter et al., Exp. Cell Res. 139:223-234 (1982). In addition, calcium phosphate has also been tested as carrier for genetic therapy to delivery large nucleic acid in vivo. Roy et al., Intl. J. Pharmaceutics 250:25, (2003).

Therapeutic calcium phosphate particles have been described. U.S. Pat. Nos. 6,355,271; 6,183,803; U.S. Pub. Nos. 2004/0258763; 2002/0054914; 2002/0068090; 2003/0185892; 2001/0048925; WO 02/064112; WO 03/051394; WO 00/46147; WO 2004/050065; Cherian et al., Drug Development and Industrial Pharmacy 26:459-463 (2000). The effect of oral formulation of insulin loaded calcium phosphate particles is tested in diabetic mice and control of blood glucose has been shown. Morcol et al., Intl. J. Pharmaceutics 277:91, (2004). The calcium phosphate particles disclosed have particle size between 300 nm to 10 um. *The animal study used particle size in the range of* 2-4 um in average. These particle sizes are clearly not optimal.

To make calcium phosphate particles with desired size, extensive sonication is required (Cherian et al. Drug Dev. Ind. Pharmacy, 26:459, 2000; Roy et al. Intl. J. Pharmaceutics 250:25, 2003), which may damage macromolecule drugs encapsulated and is not compatible to co-precipitation procedure.

Furthermore, the encapsulating efficiency of macromolecules into calcium phosphate particles is often low. For example, U.S. Pat. No. 6,355,271 discloses absorption efficiency of about 40% if insulin is added to preformed calcium phosphate particles; and about 89%, if insulin is mixed during the particle formation.

These reported methods either result in particles with less optimal size, or require harsh conditions such as extended sonication that are not compatible to macromolecule formulation. Therefore, there remains a need for oral macromolecule delivery system that is highly efficient and easily produced with low cost.

BRIEF SUMMARY OF THE INVENTION

The present invention provides a particle comprising: a) a core of calcium phosphate nano-particle; b) a biologically active macromolecule encapsulated in the core particle; and c) a surface modifying agent comprising a bile acid encapsulated in the core particle.

In some embodiments, the diameter of the core particle is less than about 1000 nm, less than about 300 nm, or less than about 200 nm.

In some embodiments, the bile acid is selected from the group consisting of cholate, deoxycholate, taurocholate, glycocholate, taurodeoxycholate, ursodeoxycholate, taurourso deoxycholate, and chenodeoxycholate.

In some embodiments, the particle further comprises an enteric coating.

In some embodiments, the biological active macromolecule is selected from the group consisting of a protein, a polypeptide, a polysaccharide, a nucleic acid, a polynucleotide, a lipid, and a carbohydrate. In some embodiments, the protein or the polypeptide is selected from the group consisting of an insulin, an erythropoietin, an interferon, a growth hormone, and a granulocyte colony-stimulating factor (G-CSF). In some embodiments, the biologically active macromolecule is an allergen selected from the group consisting of house dust mice, animal dander, molds, pollens, ragweed, latex, vespid venoms and insect-derived allergens, and any combinations thereof.

In some embodiments, the particle is adapted in the form of an aerosol. In some embodiments, the particle is adapted to deliver the biologically active macromolecule to a mucosal surface. In some embodiments, the particle is adapted to deliver the biologically active macromolecule to an ocular surface of a subject in need thereof for treatment of an ocular disease.

The invention also provides a pharmaceutical composition comprising a calcium phosphate nano-particle described herein and a pharmaceutically acceptable carrier.

The invention a method of making one or more particles of calcium phosphate, said method comprising: a) contacting an aqueous solution of a calcium salt with an aqueous solution of a phosphate salt in the presence of a surface modifying agent comprising a bile acid; b) mixing solution until calcium phosphate particles of a desired size is obtained; and c) recovering the particles.

In some embodiments, the concentration of the calcium salt is between about 5 mM and about 200 mM. In some embodiments, the concentration of the phosphate salt is between about 5 mM and about 200 mM.

In some embodiments, the method further comprises adding a biologically active macromolecule into the aqueous solution of the phosphate salt or the aqueous solution of the calcium salt before contacting the aqueous solution of the calcium salt with the aqueous solution of the phosphate salt in the presence of a surface modifying agent comprising a bile acid, whereby the calcium phosphate particle is co-crystallized with the macromolecule.

The invention also provides a method of treating a subject in need of a biologically active macromolecule, said method comprising administering a pharmaceutical composition comprising a calcium phosphate nano-particle described herein to the subject. In some embodiments, the pharmaceutical composition is administered by oral route. In some embodiments, the pharmaceutical composition is administered to a mucosal surface. In some embodiments, the pharmaceutical composition is administered to an ocular surface.

BRIEF DESCRIPTION OF THE DRAWINGS

FIG. 3 shows the image of calcium phosphate nano-particles under scanning electron microscope.

DETAILED DESCRIPTION OF THE INVENTION

The present invention provides novel calcium phosphate nano-particles encapsulated with biologically active macromolecules, methods of making the nano-particles, and methods of using the nano-particles for treating medical conditions requiring administration of the biologically active macromolecules. As used herein, "encapsulated", "embedded" or "incorporated" mean complexed, encased, bonded with, related to, coated with, layered with, or enclosed by a substance. Thus, a substance encapsulated in a particle means the substance is incorporated into the particle structure, or coated or attached to the surface of the particle, or both.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

A. Calcium Phosphate Nano-Particles with Encapsulated Biological Active Macromolecules The invention provides a calcium phosphate nano-particle comprising: a) a core of calcium phosphate nano-particle; b) a biologically active macromolecule encapsulated in the core particle; and c) a surface modifying agent comprising a bile acid encapsulated in the core particle.

The calcium phosphate core particles of the present invention have an average particle size (diameter) less than about 8000 nm, less than about 1000 nm, more preferably, less than about 300 nm. The particles may have a diameter between about 50 nm and about 8000 nm, between about 100 nm and about 3000 nm, or between about 100 nm and about 1000 nm. In some embodiments, the average particle size is less than 200 nm. In some embodiments, the average particle size is less than 100 nm.

The core particles of the present invention generally have a morphology that is generally and substantially spherical in shape and the size of the nano-particles is substantially mono-dispersed. The mono-dispersion refers to the narrow size distribution observed in these nano-particles, for example, within the range of about 20%, about 30%, about 40%, or about 50% difference in size. The surface of the particles may be substantially smooth.

The term "substantially spherical" is used herein to refer to particles that are substantially round or oval in shape, and includes particles that are unfaceted and smooth, or that have very few facets, as well as particles that are polyhedral having several or numerous facets. The term "substantially smooth" is used herein to mean essentially no surface features or irregularities having a size of 100 nm or larger. The core particles may be faceted or angular and still fall within this definition, as long as the facets do not contain many surface irregularities of the type described above.

Figure 3A:
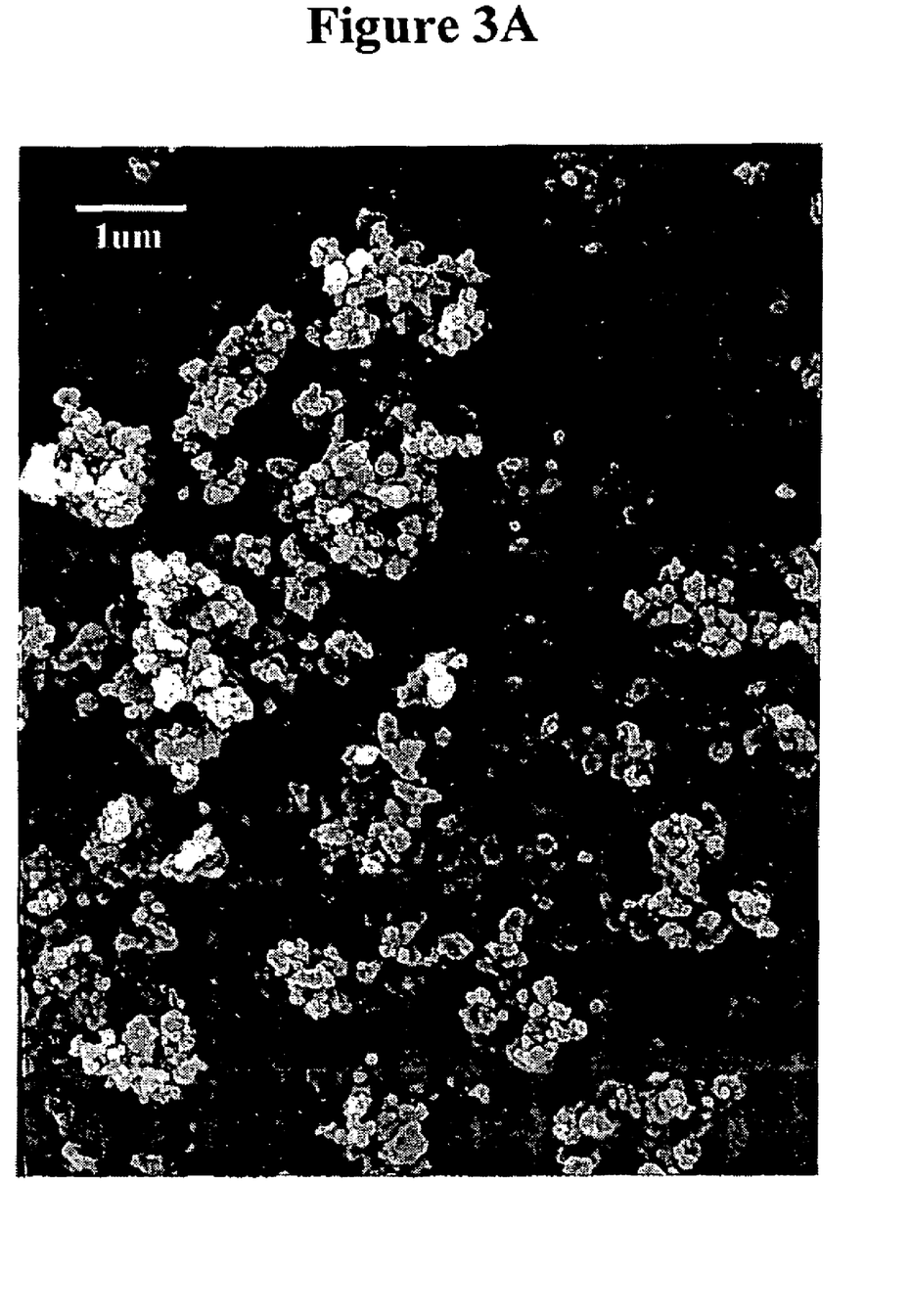
FIG. 3A shows an image of blank calcium phosphate nano-particles at 5000 fold magnification.
Figure 3B:
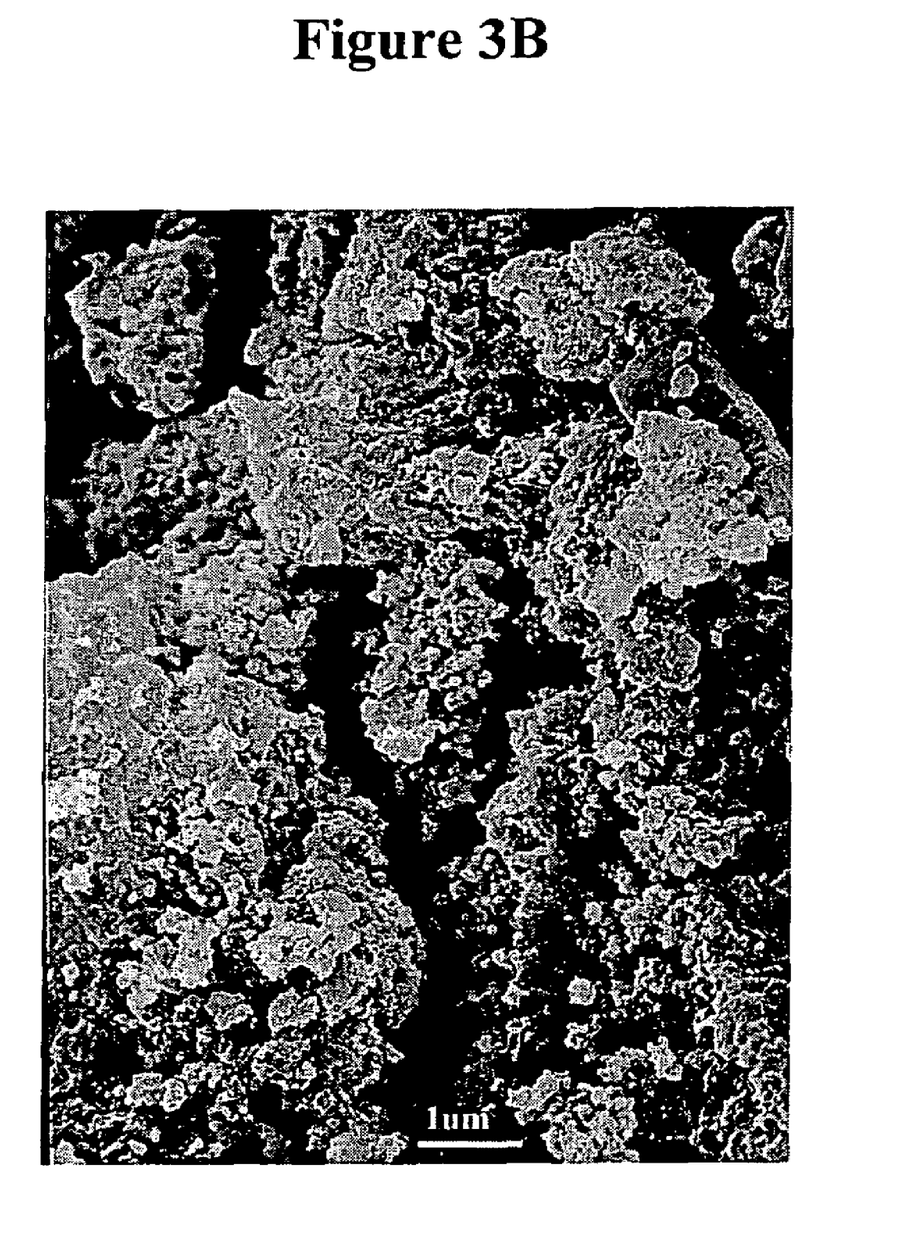
FIG. 3B shows an image of insulin loaded calcium phosphate nano-particles at 5000 fold magnification.

FIGS. 3A and 3B show the scanning electron microscopy images of examples of nano-particles prepared according to the methods described herein. FIG. 3A shows blank nano-particles without macromolecule coated or dispersed with an average diameter of about 200 nm. FIG. 3B shows the nano-particles with macromolecule insulin dispersed within the nano-particles with an average diameter of about 70 nm. Theses nano-particles demonstrate spherical shape and narrow size distribution.

The calcium phosphate nano-particles in the present invention contain a surface modifying agent comprising a bile acid which has dual function. As shown Example 1, encapsulation of biologically active macromolecules in the calcium phosphate nano-particles is enhanced when the particles are formed in the presence of a bile acid. The bile acid may also enhance bio-adhesiveness of the nano-particles and affect the size of the nano-particles. Any bile acid may be used. Examples of bile acid include, but not limited to, cholate, deoxycholate, taurocholate, glycocholate, taurodeoxycholate, ursodeoxycholate, tauroursodeoxycholate, and chenodeoxycholate.

In some embodiments, the calcium phosphate nano-particles of the present invention further comprises a polyethylene glycol (PEG). The PEG may have a molecular weight from about 500 daltons to about 20,000 daltons, e.g., about 500, about 1000, about 5000, about 10,000, about 15,000, about 20,000 daltons.

Any biologically active macromolecules may be encapsulated in the core calcium phosphate nano-particles. Such biologically active macromolecules include, but not limited to, a protein, a polypeptide, a polysaccharide, a nucleic acid, a lipid, a carbohydrate, and a combination thereof. In some embodiments, the biologically active macromolecule is an insulin, an erythropoietin, an interferon, a growth hormone, or a granulocyte colony-stimulating factor (G-CSF). In some embodiments, the biologically active macromolecule is an allergen or an antigenic material. Examples of allergen are house dust mice, animal dander, molds, pollens, ragweed, latex, vespid venoms and insect-derived allergens, and any combinations thereof.

Biologically active macromolecules include any therapeutic agents, such as alpha-1-antitrypsin, steroids, drugs to treat osteoporosis, blood coagulation factors, anti-cancer drugs, antibiotics, therapeutic antibodies, lipase, beta-blockers, anti-asthma, anti-sense oligonucleotides, DNase enzyme for respiratory and other disease, anti-inflammatory drugs, antivirals, anti-hypertensives, cardiotherapeutics such as anti-arrhythmia drugs, and gene therapies, diuretics, anti-clotting chemicals such as heparin, and combinations thereof. The agent may be a natural isolate or a synthetic, chemical or biological agent.

The calcium phosphate nano-particles may further comprises a coating. For example, the nano-particles coated and/or impregnated with biologically active macromolecules are further coated with an enteric polymer such as cellulose acetate phthalate, Eudragit, and Aquateric. The process of enteric coating has been well described in the art and references hereby are incorporated. Beyger et al., J. Pharm. Sci. 75:573-578 (1986); Maharaj et al., J. Pharm. Sci. 73:39-42 (1984).

The invention also provides calcium phosphate nano-particles comprising a core of calcium phosphate nano-particle and a biologically active macromolecule encapsulated in the core particle, wherein the average particle size (diameter) of the core particle is less than about 300 nm, with the proviso that the biologically active macromolecule is not a nucleic acid, a polynucleotide, a protein, or a polypeptide. The invention also provides calcium phosphate nano-particles comprising a core of calcium phosphate nano-particle and a biologically active macromolecule encapsulated in the core particle, wherein the average particle size (diameter) of the core particle is less than about 300 nm, and wherein the biologically active macromolecule is an antibody.

The invention also provides a pharmaceutical composition comprising a calcium phosphate nano-particle described herein and a pharmaceutically acceptable carrier. Suitable carriers and their formulations are known in the art and are described in Remington, The Science and Practice of Pharmacy 20th Ed. Mack Publishing, 2000. The pharmaceutical composition may be formulated in the form of solution, capsule, tablet, powder, and aerosol; and may be formulated in the form suitable for oral delivery, mucosal delivery, or delivery to a ocular surface. The composition may include other components, such as buffers, preservatives, nonionic surfactants, solubilizing agents, stabilizing agents, emollients, lubricants and tonicity agents. The composition may be formulated to achieve controlled release for the macromolecules.

B. Methods of Making Calcium Phosphate Nano-Particles

The invention also provides a method of making one or more particles of calcium phosphate, said method comprising: a) contacting an aqueous solution of a calcium salt with an aqueous solution of a phosphate salt in the presence of a surface modifying agent comprising a bile acid; b) mixing solution until calcium phosphate particles of a desired size is obtained; and c) recovering the particles.

The calcium phosphate nano-particles of the present invention are typically prepared as a suspension in aqueous medium by contacting a soluble calcium salt with a soluble phosphate salt, preferably, in the presence of a surface modifying agent comprising a bile acid.

In some embodiments, a distilled water solution of dibasic sodium phosphate having a concentration between about 1 mM and about 100 mM, and a surface modifying agent such as deoxycholate having a concentration of 0.01-1% (w/v) are prepared and mixed in a vessel. In some embodiments, other excipient such as polyethylene glycol having concentration of 1-30% (w/v) is also included.

The pH of the solution is controlled by the phosphate buffer system. The pH values affects the size the nano-particles and should be compatible with the stability requirement of the macromolecule to be encapsulated. The pH value may be between about 4.0 to about 9.0, or more preferably, between about 5.0 to about 8.0.

The particle size is affected by the concentrations of various components, including calcium, phosphate, and macromolecules. In general, the higher the concentration of the calcium or phosphate, the bigger the nano-particles.

To generate the nano-particles, an aqueous solution of calcium salt such as calcium chloride having a concentration between 1 mM and about 100 mM is mixed with the aqueous solution of phosphate described above. Turbidity forms immediately, indicating the formation of calcium phosphate nano-particles. Mixing is generally continued for 1 minute to 1 hour, or even longer (e.g., 2-48 hours). The size of the particles can be reduced by increasing the mixing speed or by sonication.

The calcium phosphate nano-particles generated may be further recovered and/or purified. In some embodiments, the formed calcium phosphate nano-particles having macromolecule encapsulated are recovered by centrifugation. The solution is centrifuged at 3000-1000×g for 5-15 min and collected nano-particles are dried under vacuum. In some embodiments, the formed calcium phosphate nano-particles having macromolecule encapsulated are recovered by filtration. The solution is added to a filtration device such as buchel funnel with vacuum. The filtration membrane such as 20 nm Anodisc (Whatman) can be used to recover the nano-particles, which is further dried under vacuum.

The particles of the present invention are formed in the presence of a surface modifying agent comprising a bile acid to increase the efficiency of entrapment of biologically active materials. Examples of bile acid that may be used in the present invention are cholate, deoxycholate, taurocholate, glycocholate, taurodeoxycholate, ursodeoxycholate, taurursodeoxycholate, or chenodeoxycholate. The concentration of the bile acid is generally to be from 0.01% to 5%. Generally, this procedure will result in substantially higher efficiency of coating or impregnating of the particles. For example, insulin loading efficiency in the presence of surface modifying agent can approach 100%, while only 50-60% in the absence of surface modifying agent under the same conditions.

Loading of the nano-particles with a biologically active macromolecules is preferably carried out by mixing an aqueous calcium salt solution with the biologically active macromolecule to be incorporated prior to combining and mixing with phosphate solution in the presence of a bile acid and excipients, or mixing an aqueous phosphate salt solution with the biologically active macromolecule to be incorporated prior to combining and mixing with calcium salt solution in the presence of a bile acid and excipients. The biologically active macromolecule to be encapsulated may have a concentration of about 0.1-20 mg/ml. The nano-particles are maintained for a suitable period of time, generally between one minute to one hour. The nano-particles can be separated from the suspension by either centrifugation or filtration and then dried under vacuum.

The nano-particles of the invention may be further coated, for example, with an enteric coating. The enteric coating process and materials are well known and practiced in the art. It is well recognized that selection of different enteric polymers may result in changes of targeting area of gastrointestinal tract and pharmacokinetic behavior of the macromolecules.

In some embodiments, the calcium phosphate nano-particles encapsulated with biologically active macromolecules are suspended into an enteric polymer solution. The most commonly used solvent is acetone, ethanol or combination. For example, the nano-particles can be suspend at concentration of 10-100 mg/ml. The ratio of coating polymer and core nano-particles may be between 3:1 to 0.5:1, or preferably 2:1 to 1:1. The nano-particles may be dispersed by light sonication and 1-5× volume paraffin oil may be added to the mixture. After complete mixing by vortex or sonication, 2-10× volume of chloroform may be added to solidify the coating polymer. The coated particles can be recovered by filter paper such as Whatman Chr 3MM and wash with chloroform. The recovered product may be further dried under vacuum and ground to homogenous size.

In some embodiments, the calcium phosphate nano-particles are suspended into an enteric polymer solution having a concentration between 20-100 mg/ml and the ratio of coating polymer to the nano-particles is between 2:1 to 1:1. The suspension is lightly sonicated and added directly to a solvent that does not dissolve enteric polymer and miscellable with solvent to dissolve the enteric polymer. The volume ratio between the mixture and dispersing solvent is 1:10 to 500:1. The particles are recovered by filtration onto filter paper such as Whatman Chr 3MM. The particles are dried under vacuum and ground to homogenous size.

The particles of the invention may be further coated or impregnated, or both with other surface modifying agents. Such surface modifying agents suitable for use in the present invention include substances that facilitate the binding or entrapment of biologically active macromolecules to the particle, without denaturing the macromolecule. Examples of suitable surface modifying agents are described in U.S. Pat. Nos. 5,460,830, 5,462,751, 5,460,831, and 5,219,577. Other examples of suitable surface modifying agents may include basic or modified sugars, such as cellobiose, or oligonucleotides described in U.S. Pat. No. 5,219,577. Suitable surface modifying agents also include carbohydrates, carbohydrate derivatives, and other macromolecules with carbohydrate-like components characterized by the abundance of —OH side groups, as described, for example, in U.S. Pat. No. 5,460,830. Polyethylene glycol (PEG) is a particularly suitable surface modifying agent.

Coating of calcium phosphate particles may be prepared by adding a stock solution of a surface modifying agent, such as cellobiose or PEG (e.g., around 292 mM) to a suspension of calcium phosphate core particles at a ratio of about 1 ml of stock solution to about 20 ml of particle suspension. The mixture can be swirled and allowed to stand overnight to form at least partially coated core particles. Generally, this procedure will result in substantially complete coating of the particles, although some partially coated or uncoated particles may be present.

C. Methods of Using Calcium Phosphate Nano-Particles

The invention also provides a method of treating a subject in need of a biologically active macromolecule, said method comprising administering a pharmaceutical composition comprising a calcium phosphate nano-particle described herein to the subject.

Administration of the composition of the invention may be by any means known in the art, including: orally, intravenously, subcutaneously, via inhalation, intraarterially, intramuscularly, intracardially, intraventricularly, parenteral, intrathecally, and intraperitoneally. Administration may be systemic, e.g. intravenously, or localized.

The nano-particles and pharmaceutical compositions of the present invention may be administered to a subject in need thereof. An "subject" is a mammal, more preferably a human. Mammals include, but are not limited to, farm animals (such as cows), sport animals, pets (such as cats, dogs, horses), primates, mice and rats.

In some embodiments, calcium phosphate nano-particles of the pharmaceutical composition comprise an enteric coating. Enterically coated particles may be suitably administered by oral route.

In some embodiments, the pharmaceutical composition comprises an enteric coated calcium phosphate nano-particle encapsulated with insulin. The pharmaceutical composition may be administered to a subject orally in the form of solution, capsule, tablet and powder for treating diabetes or hyperglycemia.

In some embodiments, the pharmaceutical composition comprises an enteric coated calcium phosphate nano-particle encapsulated with interferon. The pharmaceutical composition may be administered to a subject orally in the form of solution, capsule, tablet and powder for treating viral infections, cancer, and auto immune diseases.

In some embodiments, the pharmaceutical composition comprises an enteric coated calcium phosphate nano-particle encapsulated with erythropoietin. The pharmaceutical composition may be administrated to a subject orally in the form of solution, capsule, tablet or powder for treating anemia or to elevate red blood cell levels.

In some embodiments, the pharmaceutical composition comprises an enteric coated calcium phosphate nano-particle encapsulated with G-CSF. The pharmaceutical composition may be administrated to a subject orally in the form of solution, capsule, tablet or powder for treating neutropenia caused by chemotherapy or other reasons.

In some embodiments, the pharmaceutical composition comprises an enteric coated calcium phosphate nano-particle encapsulated with human growth hormone. The pharmaceutical composition may be administrated to a subject orally in the form of solution, capsule, tablet or powder to treat conditions that need growth hormone supplement such as dwarfism, adult growth hormone deficiency, wasting, and severe injuries.

In some embodiments, the pharmaceutical composition comprises an enteric coated calcium phosphate particle encapsulated with parathyroid hormone (PTH). The pharmaceutical composition may be orally administrated to a subject peroral in the form of solution, capsule, tablet and powder. The oral PTH composition may be used to treat osteoporosis or other diseases requiring PTH administration.

The particles of the present invention may be used to deliver allergens or other antigenic material. In some embodiments, the pharmaceutical composition comprises a calcium phosphate nano-particle encapsulated with an allergen or an antigen. The pharmaceutical composition may be administered to a subject for inducing an immune response in the subject, providing a controlled release of allergen to the subject, or inducing allergic desensitization in the subject. The particle may be administered subcutaneously, through inhalation, or across a mucosal surface. The particle may be delivered as a spray, an aerosol, an ointment, an eye drop, a gel, a suspension, a capsule, a suppository, an impregnated tampon, or combination thereof.

The particles of the invention may be used to deliver the biologically active macromolecules to a mucosal surface for mucosal immune protection, mucosal vaccine delivery, or mucosal drug delivery. Non-limiting examples of biologically active macromolecules include one or more of the following: antigenic material, natural immunoenhancing factors, polynucleotide material encoding immunogenic polypeptides, therapeutic drugs, such as insulin, or any other composition capable of having a therapeutic effect when administered to a mucosal surface. The particles may be complexed with any physiological acceptable excipient and administered through mucosal surfaces, such as orally, intrapulmonary, nasally, rectally, or ocularly.

The particles of the invention may be used to deliver the biologically active macromolecules to an ocular surface for treating an ocular disease. For example, therapeutic proteins or peptides or other components capable of having a therapeutic effect may be encapsulated in the particles and administered to an ocular surface. Ocular diseases or conditions that may be treated include, but not limited to, glaucoma, uveitis, retinitis pigmentosa, macular degeneration, retinopathy, retinal vascular diseases, and other vascular anomalies, endophthalmitis, infectious diseases, inflammatory but non-infectious diseases, ocular ischemia syndrome, peripheral retinal degenerations, retinal degenerations, choroidal disorders and tumors, vitreous disorders, and inflammatory optic neuropathies.

The following examples are included for illustrative purposes only and are not intend to limit the scope of the invention. Calcium phosphate nano-particles can be prepared in different embodiments as detailed in the present application. The following non-limiting examples illustrate the typical results of different embodiments.

EXAMPLES

Example 1

Fabrication of Bovine Serum Albumin (BSA) Loaded Calcium Phosphate Nano-Particles Preparation of Calcium Phosphate Particles with Sonication Two hundred milligram of polyethylene glycol (PEG, MW 10000, Fluka), 23.2 mg BSA, 1 ml of 125 mM $Na_2HPO_4$, 3 ml BBS solution (containing 1.4 mM $Na_2HPO_4$, 10 mM KCl, 12 mM Glucose, 275 mM NaCl, and 40 mM BES, pH 6.964) were dissolved into 20 ml aqueous solution. The solution had an OD280 of 0.615. Under stirring, 0.3 ml 2.5 M $CaCl_2$ was added.

Precipitation was immediately seen and the stirring was continued at room temperature for overnight. The mixture was sonicated for 15 min and spun down at 8000 rpm for 15 min. The collected particles were dried under vacuum and recovery was measured. OD280 of the supernatant was 0.084. The entrapment efficiency was estimated by the following equation:

Efficiency (%)=[1−OD280 of supernatant/OD280 of starting solution]×100

In this case the entrapment efficiency was 86%.

BSA release from the calcium phosphate particles was evaluated. Calcium phosphate particles loaded with 20.6 mg BSA were added to 20 ml phosphate buffered saline (PBS). After mixing, 22 micro-centrifuge tubes were set up for 0.8 ml aliquot each. All aliquots were rocked at 37° C. At each time point shown in Table 1 below, three tubes of aliquots were taken and spun down at 14000 rpm for 10 min. The supernatant was removed and OD280 was measured and data are shown in Table 1. BSA release from calcium phosphate particles was essentially complete in 4-8 hours in PBS.

TABLE 1

Evaluation of BSA release from calcium phosphate particles

| | Time (hour) | | | | | | |
|---|---|---|---|---|---|---|---|
| | 0.5 | 1 | 2 | 3 | 4 | 8 | 24 |
| Average OD280 | 0.059 | 0.089 | 0.154 | 0.159 | 0.183 | 0.193 | 0.174 |

Preparation of BSA-Loaded Calcium Phosphate Nano-Particles without Sonication

Two hundred milligram of polyethylene glycol (PEG, MW 10000, Fluka), 10 mg BSA, 1 ml of 125 mM $Na_2HPO_4$, 3 ml BBS solution were dissolved into 20 ml aqueous solution. The solution had OD280 of 0.350. Under stirring, 0.3 ml 2.5 M $CaCl_2$ was added.

Precipitation was immediately seen and the particles were recovered by spinning down at 8000 rpm for 15 min. The collected particles were dried under vacuum. OD280 of the supernatant was 0.224 and the estimated entrapment efficiency was 36%.

Preparation of BSA-Loaded Calcium Phosphate Nano-Particles in the Presence of Deoxycholate Two hundred milligram of polyethylene glycol (PEG, MW 10000, Fluka), 10 mg BSA, 1 ml of 125 mM $Na_2HPO_4$, 3 ml BBS solution and 40 mg deoxycholate were dissolved into 20 ml aqueous solution. OD280 was 0.296. Under stirring, 0.3 ml of 2.5 M $CaCl_2$ was added.

Precipitation was immediately seen and the particles were recovered by spinning down at 8000 rpm for 15 min. The collected particles were dried under vacuum. OD280 of the supernatant was 0.084 and the estimated entrapment efficiency was 72%.

These two examples illustrate that deoxycholate substantially enhances encapsulation efficiency under the same conditions.

Preparation of BSA-Loaded Calcium Phosphate Nano-Particles with Filtration

One gram of polyethylene glycol (PEG, MW 10000, Fluka), 40 mg BSA, 12 mM sodium phosphate, pH 6.6, and 160 mg sodium deoxycholate was dissolved in 20 ml water. Deoxycholate was dissolved into 1 ml ethanol before addition. OD280 was 1.349. Under stirring, 20 ml 72 mM $CaCl_2$ was added. After 2 min, the mixture was filtered onto an 20 nm Anodisc membrane under vacuum. The membrane was dried under vacuum and calcium nano-particles were recovered. OD280 of the filtrate was 0.142 and the encapsulation efficiency was 82%.

Example 2

Fabrication of Erythropoietin (EPO) Loaded Enteric Coated Calcium Phosphate Nano-Particles EPO sample (1 ml at 1.2 mg/ml) was dialyzed against 1 L water overnight at 4° C. and the final volume was 1.3 ml. 400 mg PEG (MW 10000, Fluka), 1.3 ml EPO, 6 ml BBS, pH 6.964, and 2 ml of 125 mM $Na_2HPO_4$ were mixed into total 40 ml solution. OD280 was 0.070. Under stirring, 600 ul of 2.5 M $CaCl_2$ was added. Precipitation was seen immediately and stirring was continued for 1 hour at room temperature.

The solution was spun down at 8000 g for 10 min to collect particles. OD280 of solution was measured to be 0.033 and all particles were dried under vacuum. The entrapment efficiency was estimated to be 53%.

EPO-loaded calcium phosphate nano-particles were coated with cellulose acetate phthalate. 30 mg EPO-loaded calcium phosphate nano-particles were suspended into 0.5 ml of 10% cellulose acetate phthalate in acetone:ethanol (95:5). 1.5 ml paraffin oil was added and mixed by vortexing, followed by addition of 6 ml chloroform. The particles were recovered with Whatman filtration paper (Chr 3 mm) and washed with chloroform. The particles were dried under vacuum and ground to homogenous size.

The EPO loading was measured by taking 1 mg particles coated calcium phosphate nano-particles and resuspended into 0.5 ml PBS at room temperature for 4 hours. After spinning down at 14000 rpm, the EPO concentration in supernatant was measured with a commercial ELISA kit (R&D System). The EPO loading was 3600 IU/mg.

Example 3

In Vivo Activity of Oral Erythropoietin (EPO) in Enteric Coated Calcium Phosphate Nano-Particles The activity of oral EPO in enteric coated calcium phosphate nano-particles was evaluated in normal BalB/c mice by measuring hematocrit.

Animals. Nine 6-8 week-old female Balb/C mice were caged in a ventilated room. Food and water were supplied ad librium. Light cycle was set for every 12 hours.

Treatment. Mice were arbitrarily divided into three groups with three mice in each group. Vehicle group was garvaged with 0.5 ml vehicle solution (10 mM sodium acetate, pH 4.0) once daily for 5 days. Subcutaneous (SC) injection group was injected with 50 IU EPO in vehicle once daily 5 days. Oral group was garvaged with 1000 IU EPO in 0.5 ml vehicle solution once daily for 5 days. All mice were given i.p. injection of 10 mg iron dextran on day 2.

On day 10, blood samples were drawn from retrobubar puncture and heparized capillary tubes were used to collected blood sample. Capillary tubes were spun down at 3000 rpm for 20 min and hematocrit (HCT) was calculated by the ratio of red blood cell fraction in total blood. The result is shown in Table 2 below. Two-tailed and unequal variance t-test was performed with built-in function in Excel spreadsheet program.

TABLE 2

HCT value in animals

| Group | Number of animals | HCT | p value compared to vehicle |
|---|---|---|---|
| Vehicle | 3 | 0.51 ± 0.01 | |
| SC | 3 | 0.52 ± 0.02 | 0.41 |
| Oral | 3 | 0.55 ± 0.01 | <0.05 |

The data suggest that oral delivered EPO in enteric coated calcium phosphate nano-particles was active and increased HCT value significantly.

Example 4

Fabrication of Enteric Coated Granulocyte Colony-Stimulating Factor (G-CSF) Loaded Calcium Phosphate Nano-Particles The duel effect of deoxycholate on encapsulation and biological activity is illustrated in the next two examples.

Fabrication of G-CSF Loaded Calcium Phosphate Nano-Particles in the Absence of Deoxycholate 20 ml G-CSF at 1.9 mg/ml sample was dialyzed against 3 L water at 4° C. overnight and the final G-CSF concentration was 1.5 mg/ml. 200 mg PEG (MW 10000, Fluka), 2.5 ml G-CSF, 3 ml BBS, pH 6.964, 1 ml of 125 mM $Na_2HPO_4$ was mixed and adjusted to 20 ml in distilled water. OD280 was 0.145. Under stirring, 300 ul of 2.5 M $CaCl_2$ was added and precipitation was seen immediately. Stirring was continued for 10 min and particles were homogenized with a polytron homogenizer for 10 min and recovered by spinning down at 8000 g for 10 min. OD280 of the supernatant was 0.033 and the encapsulation efficiency was 77%. Particles were dried under vacuum.

G-CSF loaded calcium phosphate nano-particles were coated with enteric polymer cellulose acetate phthalate. 17 mg of particles was suspended into 400 ul 10% cellulose acetate phthalate in 95:5 acetone:ethanol. After mixing by vortex, 20 ml paraffin oil was added while stirring and 7.5 ml chloroform was added after one minute. The coated particles were recovered by filtration onto Whatman filter paper (Chr 3 mm) and washed with chloroform. The coated particles were dried under vacuum and ground.

Fabrication of G-CSF Loaded Calcium Phosphate Particles in Presence of Deoxycholate 200 mg PEG (MW 10000, Fluka), 2.5 ml GCSF, 65.9 mg deoxycholate, 3 ml BBS solution, pH 6.964, and 1 ml of 125 mM $Na_2HPO_4$ was dissolved and adjusted to 20 ml. Deoxycholate was dissolved into 1 ml ethanol before addition. OD280 was 0.106. Under stirring, 300 ul of 2.5M $CaCl_2$ was added and precipitation was seen immediately. Stirring continued for 10 min, particles were homogenized with a polytron homogenizer for 5 min and recovered by spinning down at 8000 g for 10 min. OD280 of the supernatant was 0.008. The encapsulation efficiency was 92%. Particles were dried under vacuum.

G-CSF loaded calcium phosphate nano-particles were coated with enteric polymer cellulose acetate phthalate. 58 mg particles was suspended into 1.2 ml 5% cellulose acetate phthalate in 95:5 acetone:ethanol. After mixing by vortex, 20 ml paraffin oil was added while stirring and 7.5 ml chloroform was added after one minute. The coated particles were recovered by filtration onto Whatman filter paper (Chr 3 mm) and washed with chloroform. The coated particles were dried under vacuum and ground.

The examples demonstrate that entrapment efficiency can be significantly improved if particles are prepared in the presence of deoxycholate.

Example 5

In Vivo Activity of Oral G-CSF in Enteric Coated Calcium Phosphate Nano-Particles The activity of oral G-CSF was determined by counting white blood cell numbers after treatment in normal Balb/C mice.

Animals. Eighteen 6-8 week-old Balb/C mice were caged in a ventilated room. Food and water were supplied ad librium. Light cycle was set for every 12 hours.

Treatment. Mice were arbitrarily divided into four groups. Vehicle and SCG groups had four mice and CAP and CAPD groups had 5 mice, respectively. Vehicle group was treated with 0.5 ml 10 mM NaAc, pH 4.0. SCG was treated with 0.1 ml subcutaneous injection of 100 ug/kg G-CSF in vehicle. CAP group was treated with oral G-CSF in enteric coated calcium phosphate particles in 1 ml vehicle at 2 mg/kg G-CSF. CAPD was oral G-CSF in enteric coated calcium phosphate nano-particles prepared in the presence of deoxycholate. The dosage was the same as CAP group.

Mice were treated daily for 4 days and blood samples were drawn on day 5 to determine total white blood cell count. Red blood cells were lyzed and total white blood cell count was determined using a microscope. Data were analyzed using Excel spreadsheet program with built-in function of t-test.

TABLE 3

Measurement of total white blood cell counts.

| Group | Number of animals | WBC × E6 | P vs V | p vs SCG |
|---|---|---|---|---|
| Vehicle | 4 | 3.36 ± 0.82 | | |
| SCG | 4 | 5.40 ± 0.76 | <0.05 | |
| CAP | 5 | 5.74 ± 1.24 | <0.05 | 0.64 |
| CAPD | 5 | 7.42 ± 0.75 | <0.01 | <0.05 |

The data suggest that injected and oral delivered G-CSF achieved significantly higher white blood cell counts. In addition, calcium phosphate nano-particles prepared in the presence of deoxycholate delivered more G-CSF activity and achieved higher white blood cell count than that without deoxycholate.

Example 6

Bio-Equivalency of Oral G-CSF in Enteric Coated Calcium Phosphate Nano-Particles Animals. Ten 8-10 week-old Sprague-Dawley rats were caged in a ventilated room. Food and water were supplied ad librium. Light cycle was set for every 12 hours.

Treatment. Rats were arbitrarily divided into three groups, with two rats in Vehicle group (V) and four rats in injection (G) and oral G-CSF treatment (D) groups. The treatment schedule is listed in Table 4 below. V was vehicle of 10 mM NaAc, pH 4.0. G was subcutaneous injection group. D was oral G-CSF in enteric coated calcium phosphate particles prepared in the presence of deoxycholate.

TABLE 4

Treatment schedule

| Group | Route | Volume | Dose |
|---|---|---|---|
| V | Oral | 1 ml | |
| G | Subcutaneous | 100 ul | 200 ug/kg |
| D | Oral | 1 ml | 2 mg/kg |

Rats were treated and blood samples were drawn as predetermined time points at 0, 4, 8, 12, and 26 hours. Red blood cells were lyzed and total white blood cell count was determined using a microscope.

Figure 1:
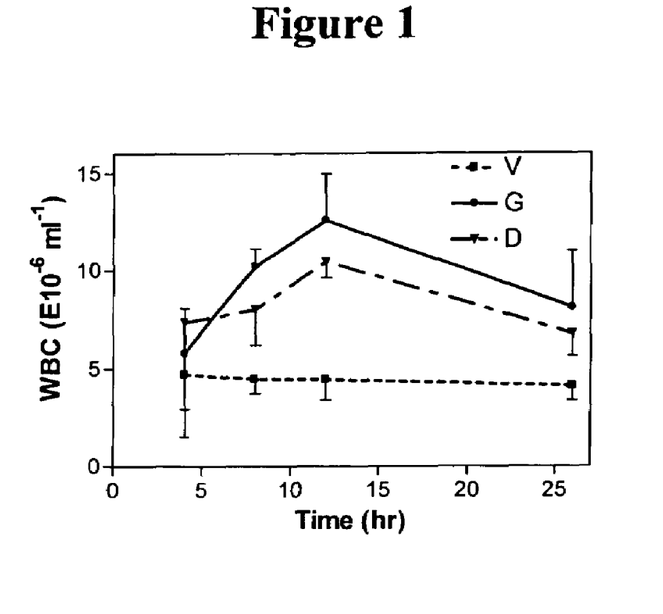
FIG. 1 is a graph showing the white blood cell counts in rats treated with vehicle ("V"), G-CSF sc injection ("G") or oral G-CSF in enteric coated calcium phosphate nano-particles ("D").

FIG. 1 shows the white blood cell counts at each time points. The area under the curve for injected and oral delivered G-CSF was estimated and bio-equivalency of oral delivered G-CSF was estimated to be 8.5% of subcutaneous route.

Example 7

Fabrication of Enteric Coated Interferon alpha (IFN) Loaded Calcium Phosphate Nano-Particles 400 mg PEG (MW 10000, Fluka), 1.3 ml IFN, 6 ml BBS solution, pH 6.964, and 2 ml 125 mM $Na_2HPO_4$ was mixed in total 40 ml aqueous solution. OD280 was 0.082. Under stirring, 600 ul 2.5 M $CaCl_2$ was added and precipitation was seen immediately. Stirring was continued for 10 min and particles were sonicated for 15 min and spun down at 8000 g for 10 min. OD280 of the supernatant was 0.033. The encapsulation efficiency was 60%. After drying under vacuum, 35.2 mg particles were recovered.

IFN loaded calcium phosphate nano-particles were coated with enteric polymer cellulose acetate phthalate. 32 mg particles was suspended into 640 ul 5% cellulose acetate phthalate in 95:5 acetone:ethanol. After mixing by vortex, 20 ml paraffin oil was added while stirring and 7.5 ml chloroform was added after one minute. The coated particles were recovered by filtration onto Whatman filter paper (Chr 3 mm) and washed with chloroform. The coated particles were dried under vacuum and ground.

Example 8

Bio-Availability of Oral IFN in Enteric Coated Calcium Phosphate Nano-Particles

Animals. Two 8-10 week-old Sprague-Dawley rats were caged in a ventilated room. Food and water were supplied ad librium. Light cycle was set for every 12 hours.

Treatment. One rat was treated with 1.6 million IU IFN via subcutaneous injection in 100 ul 10 mM NaAc, pH 4.0. The other rat was garvaged with 16 million IU IFN in calcium phosphate particles in 1 ml vehicle solution.

Blood samples were drawn as predetermined time points at −0.5, 0.5, 1, 2, 4, 6, 8, 10, 12, 16, 20, 24 hours. Serum was saved for ELISA analysis.

Figure 2:
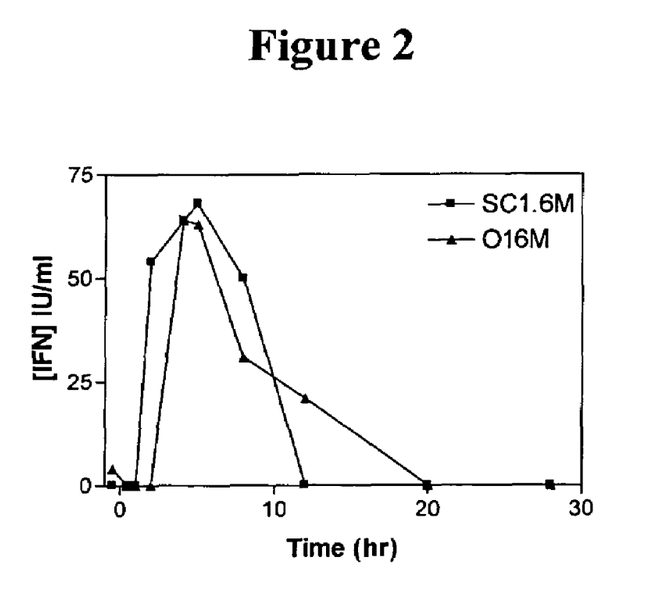
FIG. 2 is a graph showing the serum interferon concentrations in rats after treatment with interferon sc injection ("SC1.6M") or oral interferon in enteric coated calcium phosphate nano-particles ("O16M").

FIG. 2 shows the serum IFN levels at each time points. The area under the curve for injected and oral delivered IFN was estimated and bio-availability of oral delivered IFN was estimated to be 10.2% of subcutaneous route.

Example 9

Fabrication of Enteric Coated Insulin Loaded Calcium Phosphate Nano-Particles

Humulin (Eli Lilly) was purchased in a pharmacy. 180 ml insulin sample (642 mg) was exchanged into distilled water with Sephadex G-25 column (4.6 cm×100 cm, 1.7 L bed volume). OD280 was monitored and first peak was collected. Total 300 ml sample was recovered and OD280 was 2.022.

5 g PEG (MW 10000, Fluka), 600 mg insulin, 1.6 g deoxycholate, 40 ml BBS solution, pH 6.964, 19.2 ml of 125 mM $Na_2HPO_4$ was mixed and adjusted to 400 ml with distilled water. Deoxycholate was dissolved into 10 ml ethanol before addition. OD280 was 1.868. Under stirring, 400 ml of 36 mM $CaCl_2$ was mixed and particles formed were filtered onto a 20 nm Anodisc membrane immediately. OD280 of the filtrate was 0.022 and the encapsulation efficiency was 98.2%. Particles were dried under vacuum and total amount of particles recovered was 1.8 g.

Blank nano-particles were prepared with the same procedure except the omission of protein component. Both insulin loaded calcium phosphate nano-particles and blank calcium phosphate nano-particles were subject to electron scanning microcopy (SEM) examination by Material Testing Labs. The images of SEM are shown in FIGS. 3A and 3B. Blank calcium phosphate nano-particles exhibited a spherical, monodispersed and hollow morphology with average diameter 200 nm (FIG. 3A). In contrast, insulin loaded calcium phosphate nano-particles demonstrated spherical and monodispersed morphology with average diameter about 70 nm (FIG. 3B).

For enteric coating, 0.5 g insulin loaded calcium phosphate nano-particles were suspended into 5 ml acetone:ethanol (95:5) containing 0.5 g cellulose acetate phthalate. After mixing, 15 ml paraffin oil was added and mixed, followed by addition of 50 ml chloroform. The particles were collected by filtration onto Whatman filtration paper (Chr 3 mm) and washed with chloroform. Particles were dried under vacuum and ground to homogenous size. Insulin content was measured by taking release insulin from 1 mg particles in 1 ml PBS at room temperature for 3 hours. Lowry protein assay with insulin as standard was used to determine the insulin concentration in the release medium.

Example 10

Bio-Equivalency of Oral Insulin in Enteric Coating Calcium Phosphate Nano-Particles Animal Model. Thirty-five 8-10 week-old Sprague-Dawley rats were caged in a ventilated room. Food and water were supplied ad librium. Light cycle was set for every 12 hours.

Rats were injected with 60 mg/kg streptozocin ip in 20 mM Citrate buffer, pH 4.5. 1 ml of 5% glucose was given ip at 8 hours after streptozocin. After two weeks, fasting blood glucose levels were measured. Fasting blood glucose was >300 mg/Dl in 24 rats, which were used for subsequent testing.

Treatment. Sixteen rats were arbitrarily divided into three groups. Both insulin solution (OI-50, "Control") and insulin injection (SCI-5, "Injection") groups had 4 diabetic rats, respectively. The treatment group (PO-50, "Oral") had 8 rats Control group was given 50 IU insulin/kg in 0.5 ml vehicle solution orally. Injection group received sc injection with 5 IU insulin/kg in 0.5 ml vehicle. Oral group was given 50 IU insulin/kg formulated in enteric coated calcium phosphate nano-particles orally in 0.5 ml vehicle solution. Vehicle solution was 2% carboxymethyl-cellulose in 10 mM Acetic acid, pH 4.0.

TABLE 5

Insulin treatment schedule

| Group | Route | Number of animals | Volume | Dose |
| --- | --- | --- | --- | --- |
| OI-50 (Control) | Oral | 4 | 0.5 ml | 50 IU/kg |
| SCI-5 (Injection) | Subcutaneous | 4 | 0.5 ml | 5 IU/kg |
| PO-50 (Oral) | Oral | 8 | 0.5 ml | 50 IU/kg |

After fasting overnight, rats were treated and blood samples were drawn via tail vein at time points of 0, 1, 3, 6, 12, and 24 hours. Blood glucose was measured with a Glucometer (SureStep).

Figure 4:
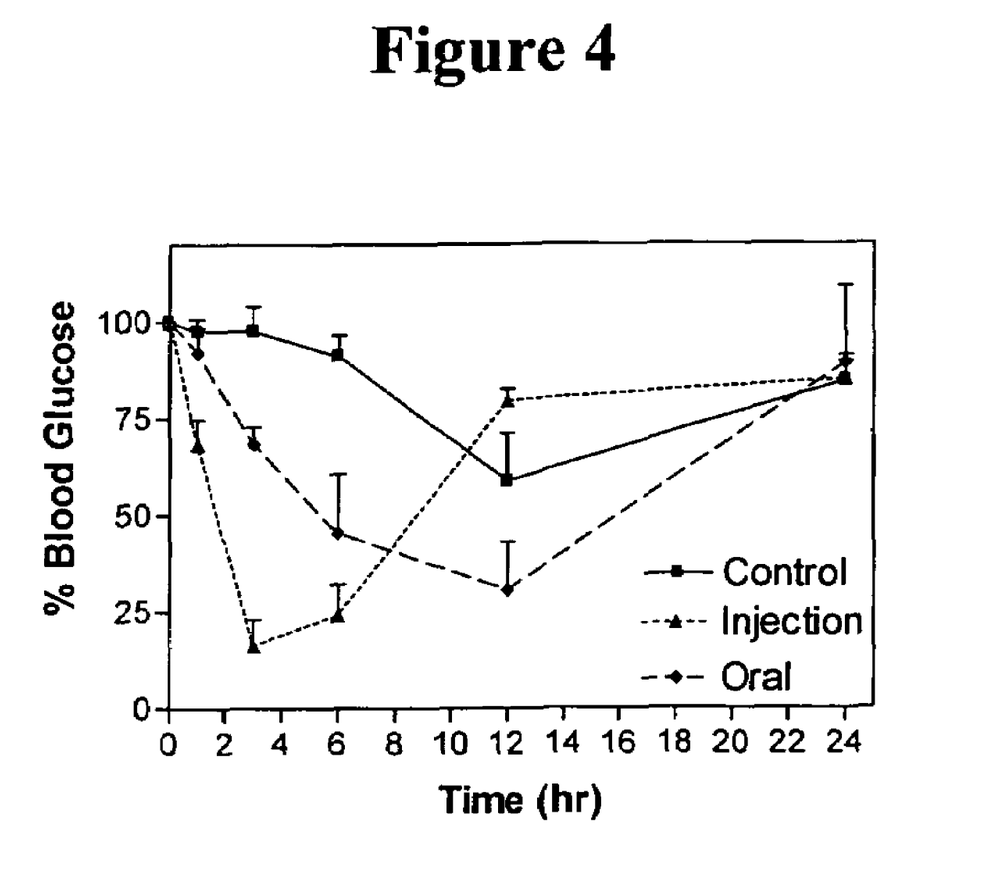
FIG. 4 is a graph showing the percent blood glucose change in diabetic rats treated with oral insulin solution ("Control"), subcutaneous insulin injection ("Injection") and oral insulin in enteric coated calcium phosphate nano-particles ("Oral").

FIG. 4 shows the percent blood glucose change at each time point after treatment with oral or subcutaneous insulin in diabetic rats. Subcutaneous insulin lowered blood glucose level quickly and return to normal within 12 hours. Oral insulin delivered with calcium phosphate particles showed more gradual and prolonged blood glucose reduction effect. The bio-equivalency of oral insulin was 12% compared with subcutaneous insulin.

Example 11

Reduction of Blood Glucose in Healthy Volunteers by Oral Insulin in Enteric Coated Calcium Phosphate Nano-Particles To assess the activity of oral insulin in enteric coated calcium phosphate nano-particles, two healthy human volunteers were tested. The standard glucose tolerance test was performed. Each volunteer was fasted for more than 12 hours and ingested 68 g glucose. The blood glucose was measured with a SureStep glucometer at −30, 0, 30, 60, 90, 120, 150, and 180 min regarding to glucose ingestion. Two cycles of measurement were performed for each volunteer. The first cycle was the standard glucose tolerance test to establish the baseline. Each volunteer took 200 U oral insulin in enteric coated calcium phosphate nano-particles at −30 min during the second measurement cycle.

Figure 5A:
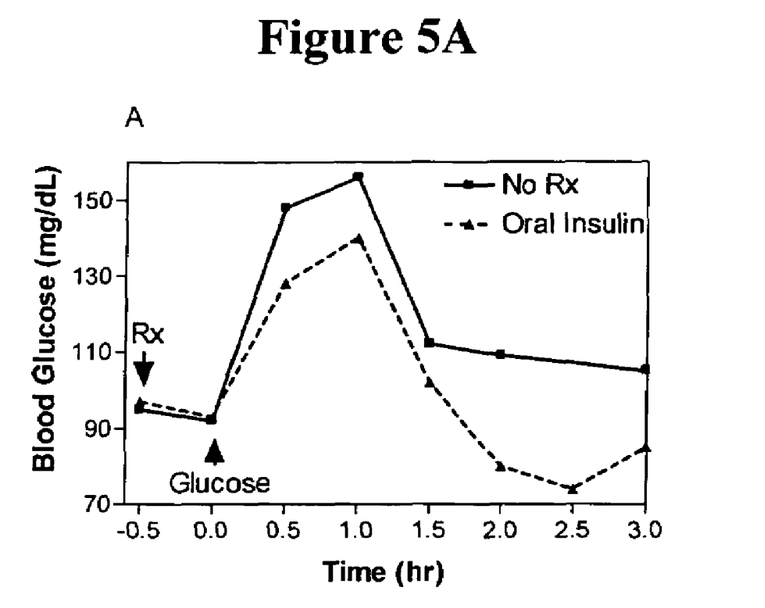
FIG. 5A is a graph showing the blood glucose change in healthy volunteer one after 68 g oral glucose ingestion with ("Oral Insulin") or without ("No Rx") 200 IU oral insulin in enteric coated calcium phosphate nano-particles.

The blood glucose change in the first volunteer is shown in FIG. 5A. Oral insulin delivered via enteric coated calcium phosphate nano-particles reduced both the peak and trough blood glucose levels.

Figure 5B:
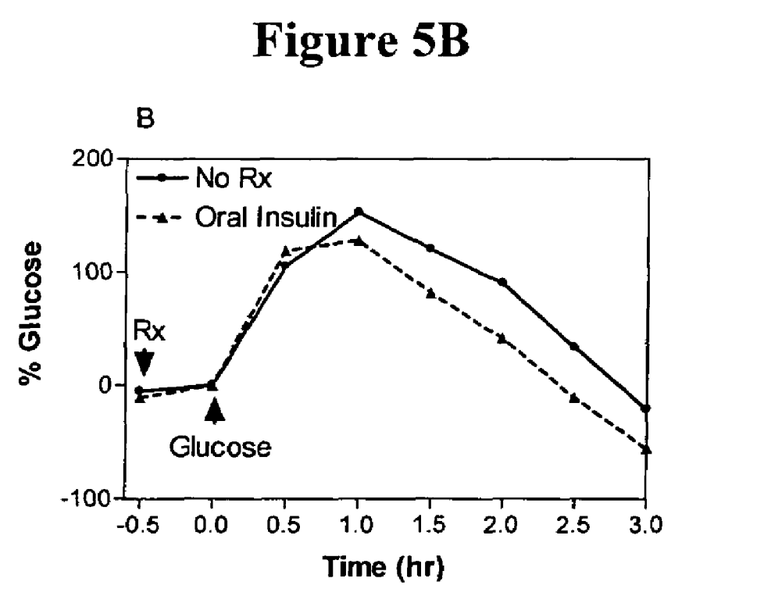
FIG. 5B is a graph showing the percent blood glucose change in healthy volunteer two after 68 g oral glucose ingestion with ("Oral Insulin") or without ("NoRx") 200 IU oral insulin in enteric coated calcium phosphate nano-particles.

The percent blood glucose change in the second volunteer is shown in FIG. 5B. Oral insulin delivered via enteric coated calcium phosphate nano-particles reduced the peak blood glucose level and depressed the blood glucose curve throughout the measurement period.

This study shows that oral insulin in enteric coated calcium phosphate nano-particles are active in human subjects and may reduce blood glucose. No adverse reactions were recorded during the measurement.

Example 12

Control of Fasting Blood Glucose of Diabetic Patients by Oral Insulin in Enteric Coated Calcium Phosphate Nano-Particles The feasibility of the oral insulin in enteric coated calcium phosphate nano-particles was further evaluated in diabetic patients. Nineteen type II diabetic patients who were regularly on insulin treatment to control their blood glucose levels volunteered for the study. Three cycles of evaluation were performed for each patient.

In the first cycle, each patient was fasted for more than 12 hours. The blood glucose levels were measured the next morning for every 30 min. A SureStep glucometer was used to determine the blood glucose level. No treatment was performed in this cycle to establish the baseline.

In the second cycle, each patient was fasted for more than 12 hours. The blood glucose levels were measured the next morning for every 30 min. A SureStep glucometer was used to determine the blood glucose level. Each patient was given 10 IU Humulin subcutaneous injection at time 0 in this cycle.

In the third cycle, each patient fasted for more than 12 hours. The blood glucose levels were measured the next morning for every 30 min. A SureStep glucometer was used to determine the blood glucose level. Either 100 IU or 200 IU oral insulin in enteric coated calcium phosphate nano-particles were given to each patient at time 0 in this cycle.

The sequence of measurement for each patient was arbitrary and there was a 48 hour wash period after oral insulin measurement before next cycle. After the study, there are 17 usable patient data for baseline measurement, 19 patient data for insulin injection, 6 patient data for 100 IU oral insulin treatment and 11 patient data for 200 IU oral insulin treatment.

Figure 6:
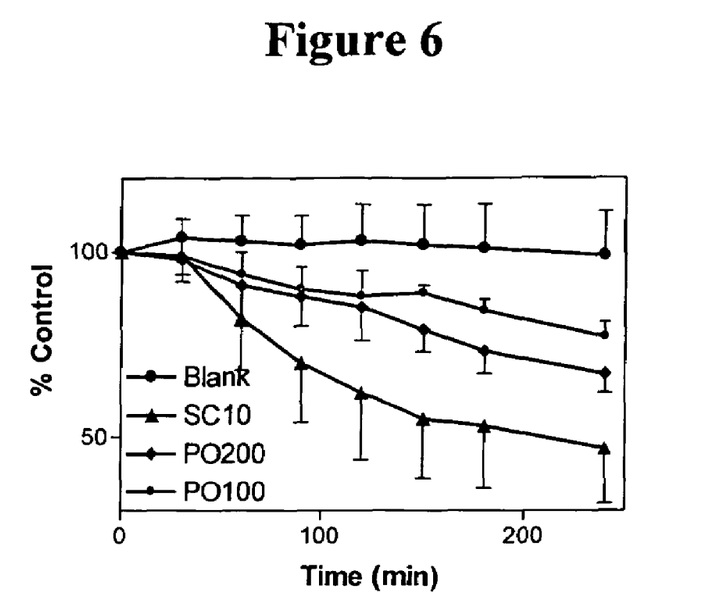
FIG. 6 is a graph showing the percent blood glucose change in volunteers with diabetes with no treatment ("Blank"), 10 IU insulin injection ("SC10"), or 100 IU ("PO100") or 200 IU ("PO200") oral insulin in enteric coated calcium phosphate nano-particles.

The percent blood glucose change each cycle of measure is shown in FIG. 6. Without treatment, blood glucose level were elevated and maintained relatively stable during the observation period. Insulin injection produced drastic reduction of blood glucose. In fact, 7 patients developed hypoglycemia and their blood glucose levels dropped below 50 mg/dL and had to be treated with oral glucose. In contrast, patient who took 100 IU or 200 IU oral insulin showed gradual yet statistically significant reduction of blood glucose level compared with baseline and no hypoglycemia was observed. In addition, patients treated with 200 IU oral insulin showed bigger reduction of blood glucose.

This study shows that oral insulin in enteric coated calcium phosphate nano-particles can effectively and dose-dependently control blood glucose level in diabetic patients.

Example 13

Fabrication of Enteric Coated Human Growth Hormone (hGH) Loaded Calcium Phosphate Nano-Particles hGH sample was exchanged into distilled water with Sephadex G25 desalting column. The amount of hGH was calculated with OD280 measurement and optic coefficient of 0.68. 200 mg PEG (MW 10000, Fluka), 84 mg hGH, 12 mM phosphate, and 320 mg deoxycholate was dissolved into 40 ml solution. OD280 was determined as 1.307. Under stirring, 40 ml of 72 mM $CaCl_2$ was mixed and precipitation was filtered onto 20 nm Anodisc membrane (Whatman) immediately. OD280 of the filtrate was 0.039. Particles were dried under vacuum and the entrapment efficiency was 95% based on the OD280 measurement before and after particle formation.

For enteric coating, 300 mg hGH loaded calcium phosphate nano-particles were suspended into 4 ml 10% cellulose acetate phthalate in 95:5 acetone:ethanol. After mixing, 6 ml paraffin oil was added and mixed, followed by 18 ml chloroform. The particles were filtered onto Whatman paper (Chr 3 mm) and washed with chloroform. Particles were dried under vacuum and ground to homogenous size.

hGH content was measured by adding 1 mg particles into 1 ml PBS and incubating at room temperature for 3 hours. Lowry protein assay with hGH as standard was used to determine the hGH concentration in the release medium Example 14

Promotion of Body Weight Gain by Oral Human Growth Hormone in Enteric Coated Calcium Phosphate Nano-Particles The activity of oral hGH in enteric coated calcium phosphate nano-particles was tested in hypophysectomized rats, a standard assay for growth hormone activity.

Animal Model. Twenty 6 week-old Sprague-Dawley rats undergone hypophysectomy surgery (Taconic Farms) were caged in a ventilated room. Food and water were supplied ad libitum. Light cycle was set for every 12 hours. Body weight of each rat was monitored daily.

Treatment. Twenty rats were arbitrarily divided into three groups. There were four rats in Vehicle and Injection groups, respectively. The treatment group had 12 rats. Vehicle group was treated with paraffin oil. Rats were treated each morning and body weights were measured each evening.

TABLE 5

| hGH treatment schedule | | | | |
| --- | --- | --- | --- | --- |
| Group | Route | Number of animals | Volume | Dose |
| V | Oral | 4 | 0.5 ml | |
| SC20 | Subcutaneous | 4 | 0.5 ml | 20 ug/rat/day |
| PO50 | Oral | 12 | 0.5 ml | 50 ug/rat/day |

Figure 7:
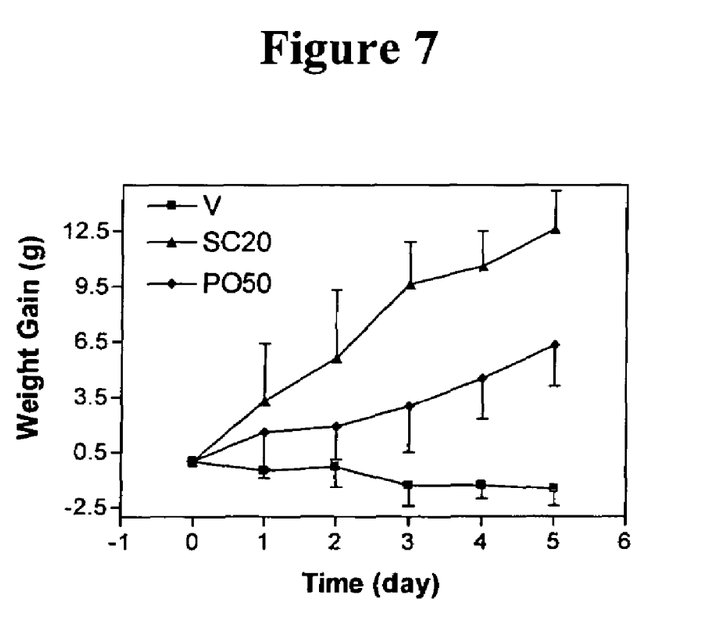
FIG. 7 is graph showing the net body weight gain in hypophysectomized rats treated with vehicle ("V"), growth hormone injection ("SC20") or oral growth hormone in enteric coated calcium phosphate nano-particles ("PO50").

FIG. 7 shows the net body weight gain after treatment with oral or subcutaneous hGH in hypophysectomized rats. Subcutaneous hGH resulted in substantial net body weight gain while Vehicle treatment produce slightly reduction of body weight. Oral hGH delivered with enteric coated calcium phosphate nano-particles produced significant body weight, indicating that oral hGH in enteric coated calcium phosphate nano-particles is biologically active.

Example 15

Fabrication of Parathyroid Hormone (PTH) Loaded Calcium Phosphate Nano-Particles Parathyroid hormone 1-34 (PTH) was exchanged into distilled water with Sephadex G25 desalting column. 400 mg PEG (MW 10000, Fluka), 6 ml BBS solution, pH 6.964, and 2 ml 125 mM of $Na_2HPO_4$ was mixed in 40 ml solution. OD280 was determined as 0.082. Under stirring, 600 ul 2.5M $CaCl_2$ was added. Precipitation was seen immediately and particles were spun down at 8000 g for 10 min. OD280 of the supernatant was 0.033. Particles were dried under vacuum. The entrapment efficiency was estimated to be 59% based on the OD280 measurement before and after particle formation.

Example 16

Fabrication of Polysaccharide & Nucleic Acid Extract of BCG Loaded Calcium Phosphate Nano-Particles The polysaccharide and nucleic acid extract of Bacillus Calmette-Guerin (BCG-PSN) has immune modulating activity. BCG-PSN contains both polysaccharide and nucleic acid and is used to demonstrate the utility of calcium phosphate nano-particles in this class of compounds.

BCG-PSN was obtained in powder form from Chengdu Rongsheng Pharmaceutical Ltd. (Chengdu, China). 1 mg BCG-PSN, 50 mg PEG (Fluka, MW 10000), 0.25 ml BBS, pH 6.964, and 0.75 ml 125 mM $Na_2HPO_4$ was mixed in 20 ml solution. OD260 was 0.22 and polysaccharide content was measured by Anthrone method.

Under stirring, 75 ul 5 M $CaCl_2$ was added and stirring was continued at room temperature for 1 hour. Particles were spun down at 8000 g for 10 min. OD260 of the supernatant was 0.0 and polysaccharide concentration was 22.1 ug/ml. The capsulation efficiency was 100% for nucleic acid component and about 63% for polysaccharide component. Particles were dried under vacuum.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

REFERENCES

U.S. Pat. Nos. 3,925,545; 4,016,252; 4,350,686; 4,500,512; 4,552,756; 5,178,882; 5,219,577; 5,306,508; 5,334,394; 5,364,838; 5,460,830; 5,460,831; 5,462,750; 5,462,751; 5,464,634; 5,506,203; 5,549,973; 5,580,859; 5,593,875; 5,595,762; 5,620,896; 5,629,021; 5,641,515; 5,648,097; 5,695,617; 5,747,001; 5,785,975; 5,827,822; 5,866,553; 5,891,420; 5,898,028; 5,902,789. FR Pat. Nos. 7212036; 7924948. GB Pat No. 1422973. PCT WO 90/11092; WO 93/17706; WO 93/24640; WO98/35562; WO00/15194; WO 00/46147.

Academic Press Dictionary of Science and Technology. http://www.harcourt.com/dictionary/def/2/2/3/1/2231200.html, November 2000.*

Abstracts of Papers Presented at the 1992 meeting on Modern Approaches to New Vaccines, Including Prevention of AIDS, Cold Spring Harbor), Vaccine 11: 92 (1993).

Aldovini and R. A. Young, "Humoral and cell-mediated immune responses to live recombinant BCG-HIV vaccines," Nature 351: 479-482 (1991).

Ascadi et al., "Human dystrophin expression in mdx mice after intramuscular injection of DNA constructs," Nature 352: 815-818 (1991).

Bartus et al., "Sustained Delivery of Proteins for Novel Therapeutic Products," Science, 281(5380): 1161-1162 (1998).

Bastin, et al., "Use of Synthetic Peptides of Influenza Nucleoprotein to Define Epitopes Recognized by Class I-Restricted Cytotoxic T Lymphocytes," J. Exp. Med., 165(4): 1508-1523 (1987).

Benvenisty, N., and Reshef L. PNAS 83, 9551-9555, (1986).

Bennink and J. W. Yewdell, "Recombinant Vaccinia Viruses as Vectors for Studying T Lymphocyte Specificity and Function," Curr. Top. Microbiol. Immunol., 163:153-184 (1990). Carbone and Bevan, "Induction of Ovalbumin-specific cytotoxic T cells by in vivo peptide immunization," J. Exp. Med., 169(1): 603-612 (1989).

Collins et al., "Processing of exogenous liposome-encapsulated antigens in vivo generates class I MCH-restricted T cell responses," J. Immunol., 148(11): 3336-3341 (1992).

Cooney et al., "Safety of and immunological response to a recombinant vaccinia virus vaccine expressing HIV envelope glycoprotein," Lancet, 337: 567-572 (1991).

Cox et al., "Bovine Herpesvirus 1: Immune Responses in Mice and Cattle Injected with Plasmid DNA," 1993, J. Virol., 67(9): 5664-5667.

Deres, et al., "In vivo priming of virus-specific cytotoxic T lymphocytes with synthetic lipoprotein vaccine," Nature, 342: 561-564 (1989).

Donnelly et al., "DNA Vaccines," Annu. Rev. Immunol., 15: 617-648 (1997).

Edgington, "Turning On Tumor-Fighting T-Cells," Biotechnology, 11:1117-1119 (1993).

Edwards et al., Science, 276:1868 (1997).

Friedman, T., "Progress toward human gene therapy," Science, 244, 1275-1281 (1989).

Furth et al., "Gene Transfer into Somatic Tissues by Jet Injection," Analytical Biochemistry, 205(2): 365-368, (1992).

Gardner et al., "Cell-mediated cytotoxicity against ectromelia virus-infected target cells," Eur. J. Immunol., 4: 68-72 (1974).

Goto et al., "Local tissue irritating effects and adjuvant activities of calcium phosphate and aluminum hydroxide with different physical properties," Vaccine, 15(12/13):1364-1371 (1997).

Hahn et al., "Infectious Sindbis virus transient expression vectors for studying antigen processing and presentation," Proc. Natl. Acad. Sci. (USA) 89: 2679-2683 (1992).

Hansen et al., FEBS Lett. 290, 73 (1991).

Jiao et al., Hum. Gene Therapy 3, 21 (1992) *.

Kato et al., "Relationship between Hemolytic Activity and Adsorption Capacity of Aluminum Hydroxide and Calcium Phosphate as Immunological Adjuvants for Biologicals," Microbiol. Immunol., 38(7): 543-548 (1994).

Kitsis et al., "Hormonal modulation of a gene injected into rat heart in vivo," Proc. Natl. Acad. Sci. (USA) 88: 4138-4142 (1991).

Lin et al., "Expression of Recombinant Genes in Myocardium In Vivo after Direct Injection of DNA," Circulation 82(6): 2217-2221 (1990).

Lin and Askonas, "Biological properties of an influenza A virus-specific killer T cell clone," J. Exp. Med. 154(1): 225-234 (1981).

Maniatis, et al., Molecular Cloning, Cold Spring Harbor Laboratory Press, New York, 1.0-19.0 (1989).

Mascola et al., "Surveillance of Listeriosis in Los Angeles County, 1985-1986," Arch. Intern. Med., 149(7): 1569-1572 (1989).

McMichael et al., "Cytotoxic T-Cell Immunity to Influenza," New Engl. J. Med., 309(1): 13-17 (1983).

McMichael et al., "Recognition of Influenza A virus Nucleoprotein by human cytotoxic T lymphocytes," J. Gen. Virol., 67: 719-726 (1986).

Miller, "Retroviral Vectors," Curr. Top. Microbiol. Immunol., 158, 3-24 (1992).

Montgomery, D. L. et al., 1993, Cell Biol., 12, pp. 777-783. *.

Redfield et al., "Disseminated Vaccinia in a Military Recruit with Human Immunodeficiency Virus (HIV) Disease," New Engl. J. Med., 316(11): 673-676 (1987).

Robinson et al., "Protection against a lethal influenza virus challenge by immunization with a haemagglutinin-expressing plasmid DNA," Vaccine 11(9): 957-960 (1993).

Sato et al., "Immunostimulatory DNA Sequences Necessary for Effective Intradermal Gene Immunization," Science 273: 352-354 (1996).

Schafer et al., "Induction of a cellular immune response to a foreign antigen by a recombinant *Listeria* monocytogenes vaccine," J. Immunol., 149(1):53-59 (1992).

Service, Science 277:5330 (1997).

Stover et al., "New use of BCG for recombinant vaccines," Nature 351: 456-460 (1991).

Takahashi et al., "Induction of CD8 cytotoxic T cells by immunization with purified HIV-1 envelope protein in ISCOMs," Nature, 344: 873-875 (1990).

Tang et al., "Genetic immunization is a simple method for eliciting an immune response," Nature, 356: 152-154 (1992).

Taylor and Askonas, "Influenza nucleoprotein-specific cytotoxic T-cell clones are protective in vivo," Immunol., 58(1): 417-420 (1986).

Townsend, "Antigen recognition by class I-restricted T lymphocytes," Annu. Rev. Immunol., 7: 601-624 (1989).

Townsend et al., "The Epitopes of Infulenza Nucleoprotein Recognized by Cytotoxic T Lymphocytes Can Be Defined with Short Synthetic Peptides," Cell 44: 959-968 (1986).

Ulmer, J. B. et al., "Heterologous Protection Against Influenza by Injection of DNA Encoding a Viral Protein," Science, 259: 1745-1749 (1993).

Wang et al., "Gene inoculation generates immune responses against human immunodeficiency virus type I," P.N.A.S. USA 90: 4156-4160 (May, 1993).

Wang, et al., "Enhanced type I immune response to a hepatitis B DNA vaccine by formulation with calcium- or aluminum phosphate," Vaccine, 18: 1227-1235 (2000).

Weiner et al., "Immunostimulatory oligodeoxynucleotides containing the CpG motif are effective as immune adjuvants in tumor antigen immunization," PNAS (USA) 94(19): 10833-10837 (1997).

Wolff et al., "Long-term persistence of plasmid DNA and foreign gene expression in mouse muscle," Human Mol. Genet. 1(6): 363-369 (1992).

Wolff et al., "Direct Gene Transfer into Mouse Muscle in Vivo," Science 247: 1465-1468 (1990).

Yap and Ada, "Transfer of specific cytotoxic T lymphocytes protects mice inoculated with influenza virus," Nature, 273: 238-239 (1978).

Yewdell et al., "Influenza A virus nucleoprotein is a major target antigen for cross-reactive anti-influenza A virus cytotoxic T lymphocytes," Proc. Natl. Acad. Sci. (USA) 82: 1785-1789 (1985).

Zhu et al., "Systemic Gene Expression After Intravenous DNA Delivery into Adult Mice," Science 261: 209-211 (1993).

The invention claimed is:

1. A plurality of particles, each particle comprising:
   a) a core calcium phosphate nanoparticle;
   b) a biologically active macromolecule encapsulated in the core nanoparticle; and
   c) a surface modifying agent comprising a bile salt encapsulated in the core nanoparticle,
   wherein the average diameter of the core nanoparticles is about 200 nm or less.

2. The particles of claim 1, wherein the bile salt is selected from the group consisting of cholate, deoxycholate, taurocholate, glycocholate, taurodeoxycholate, ursodeoxycholate, tauroursodeoxycholate, and chenodeoxycholate.

3. The particles of claim 1, further comprising an enteric coating.

4. The particles of claim 1, wherein the biologically active macromolecule is selected from the group consisting of a protein, a polypeptide, a polysaccharide, a nucleic acid, a polynucleotide, a lipid, and a carbohydrate.

5. The particles of claim 4, wherein the protein or the polypeptide is selected from the group consisting of an insulin, an erythropoietin, an interferon, a growth hormone, and a granulocyte colony-stimulating factor.

6. The particles of claim 3, wherein the biologically active macromolecule is selected from the group consisting of an insulin, an erythropoietin, an interferon, a growth hormone, and a granulocyte colony-stimulating factor.

7. The particles of claim 1, wherein the particles are formulated as an aerosol.

8. The particles of claim 1, wherein the particles are adapted to deliver the biologically active macromolecule to a mucosal surface.

9. The particles of claim 1, wherein the particles are adapted to deliver the biologically active macromolecule to an ocular surface of a subject in need thereof for treatment of an ocular disease.

10. A pharmaceutical composition comprising the particles of claim 1 and a pharmaceutically acceptable carrier.

11. A pharmaceutical composition comprising the particles of claim 3 and a pharmaceutically acceptable carrier.

12. A pharmaceutical composition comprising the particles of claim 6 and a pharmaceutically acceptable carrier.

13. A method of making a plurality of calcium phosphate particles, said method comprising:
   a) contacting an aqueous solution of a calcium salt with an aqueous solution of a phosphate salt in the presence of a surface modifying agent comprising a bile salt at a concentration ranging from 0.01% to 5%;
   b) mixing resulting solution until calcium phosphate particles having an average diameter of about 200 nm or less are obtained; and
   c) recovering the particles.

14. The method of claim 13, wherein the concentration of the calcium salt is between about 5 mM and about 200 mM.

15. The method of claim 13, wherein the concentration of the phosphate salt is between about 5 mM and about 200 mM.

16. The method of claim 13, further comprising adding a biologically active macromolecule into the aqueous solution of the phosphate salt or the aqueous solution of the calcium salt before contacting the aqueous solution of the calcium salt with the aqueous solution of the phosphate salt in the presence of a surface modifying agent comprising a bile salt, whereby the calcium phosphate particle is co-crystallized with the biologically active macromolecule, and wherein the encapsulation of the biologically active macromolecule into the calcium phosphate particle is enhanced compared to a calcium phosphate particle that does not contain the bile salt.

17. The method of claim 13, wherein the bile salt is selected from the group consisting of cholate, deoxycholate, taurocholate, glycocholate, taurodeoxycholate, ursodeoxycholate, tauroursodeoxycholate, or chenodeoxycholate.

18. A method of treating a subject in need of a biologically active macromolecule, said method comprising administering the pharmaceutical composition of claim 10 to the subject.

19. The particles of claim 1, wherein the particles are adapted for oral delivery of the biologically active macromolecule.

20. The method of claim 18, wherein the pharmaceutical composition is administered to the subject by oral route.

21. The method of claim 16, wherein the encapsulation efficiency of the biologically active macromolecule into the calcium phosphate particles is greater than about 80%.

22. The method of claim 16, wherein the encapsulation efficiency of the biologically active macromolecule into the calcium phosphate particles is greater than about 90%.

23. The method of claim 16, wherein the encapsulation efficiency of the biologically active macromolecule into the calcium phosphate particles is greater than about 95%.

24. A method of treating a subject in need of a biologically active macromolecule, said method comprising administering the pharmaceutical composition of claim 11 to the subject.

25. A method of treating a subject in need of a biologically active macromolecule, said method comprising administering the pharmaceutical composition of claim 12 to the subject.

* * * * *